(12) United States Patent
Chin et al.

(10) Patent No.: US 11,504,246 B2
(45) Date of Patent: *Nov. 22, 2022

(54) ARTIFICIAL DISK WITH SENSORS

(71) Applicant: AXIOMED, LLC, Malden, MA (US)

(72) Inventors: Kingsley Chin, Fort Lauderdale, FL (US); Jeremy Crossgrove, Brookline, MA (US); Jake Lubinski, Beverly, MA (US)

(73) Assignee: AXIOMED, LLC, Malden, MA (US)

( * ) Notice: Subject to any disclaimer, the term of this patent is extended or adjusted under 35 U.S.C. 154(b) by 99 days.

This patent is subject to a terminal disclaimer.

(21) Appl. No.: 17/014,286

(22) Filed: Sep. 8, 2020

(65) Prior Publication Data

US 2021/0052394 A1 Feb. 25, 2021

Related U.S. Application Data

(63) Continuation of application No. 16/148,579, filed on Oct. 1, 2018, now Pat. No. 10,765,527.
(Continued)

(51) Int. Cl.
*A61F 2/44* (2006.01)
*A61F 2/30* (2006.01)
(Continued)

(52) U.S. Cl.
CPC ............. *A61F 2/442* (2013.01); *A61F 2/482* (2021.08); *A61F 2002/30065* (2013.01);
(Continued)

(58) Field of Classification Search
CPC .............. A61F 2/442; A61F 2002/4666; A61F 2002/4672; A61F 2002/30546;
(Continued)

(56) References Cited

U.S. PATENT DOCUMENTS

| 5,556,092 A | 9/1996 | Theken |
|---|---|---|
| D377,895 S | 2/1997 | Theken et al. |

(Continued)

FOREIGN PATENT DOCUMENTS

| CN | 101674788 | 3/2010 |
|---|---|---|
| CN | 204542473 | 8/2015 |
| CN | 106806040 | 6/2017 |

OTHER PUBLICATIONS

International Search Report and Written Opinion dated Dec. 13, 2018 issued in corresponding International Application No. PCT/US18/53730.
(Continued)

*Primary Examiner* — Javier G Blanco
(74) *Attorney, Agent, or Firm* — Onello & Mello, LLP

(57) ABSTRACT

A prosthetic disc can take the form of a sensing artificial disc that includes a resilient core and at least one sensor configured to sense one or more conditions within and/or experienced by the disc. The sensing artificial disc can serve as a replacement to a failed or injured disc between two vertebrae of a spine. The sensing artificial disc can include at least one element configured to change a condition or property of the resilient core in response to a condition sensed by the at least one sensor. A prosthetic disc can include therapeutic system configured to deliver medication to the body, which can include a reservoir of medication.

18 Claims, 9 Drawing Sheets

Related U.S. Application Data

(60) Provisional application No. 62/565,357, filed on Sep. 29, 2017.

(51) Int. Cl.
*A61F 2/46* (2006.01)
*A61F 2/48* (2006.01)

(52) U.S. Cl.
CPC ............ *A61F 2002/3067* (2013.01); *A61F 2002/3068* (2013.01); *A61F 2002/30069* (2013.01); *A61F 2002/30079* (2013.01); *A61F 2002/30462* (2013.01); *A61F 2002/30546* (2013.01); *A61F 2002/30563* (2013.01); *A61F 2002/30668* (2013.01); *A61F 2002/4666* (2013.01); *A61F 2002/4672* (2013.01)

(58) Field of Classification Search
CPC .... A61F 2002/30563; A61F 2002/3067; A61F 2250/0002
See application file for complete search history.

(56) References Cited

U.S. PATENT DOCUMENTS

| | | | |
|---|---|---|---|
| 6,228,085 B1 | 5/2001 | Theken et al. |
| 6,342,055 B1 | 1/2002 | Eisermann et al. |
| 6,447,448 B1 | 9/2002 | Ishikawa et al. |
| 6,607,558 B2 | 8/2003 | Kuras |
| 7,001,389 B1 | 2/2006 | Navarro et al. |
| 7,128,761 B2 | 10/2006 | Kuras et al. |
| 7,169,181 B2 | 1/2007 | Kuras |
| 7,278,997 B1 | 10/2007 | Mueller et al. |
| 7,491,209 B2 | 2/2009 | Mueller et al. |
| 7,531,002 B2 | 5/2009 | Sutton et al. |
| 7,588,600 B2 | 9/2009 | Benzel et al. |
| 7,695,517 B2 | 4/2010 | Benzel et al. |
| 7,763,075 B2 | 7/2010 | Navarro et al. |
| 7,763,076 B2 | 7/2010 | Navarro et al. |
| 7,766,911 B1 | 8/2010 | Navarro et al. |
| 7,771,478 B2 | 8/2010 | Navarro et al. |
| 7,771,480 B2 | 8/2010 | Navarro et al. |
| 7,780,666 B1 | 8/2010 | Navarro et al. |
| 7,785,327 B1 | 8/2010 | Navarro et al. |
| 7,794,499 B2 | 9/2010 | Navarro et al. |
| 7,806,935 B2 | 10/2010 | Navarro et al. |
| 7,824,444 B2 | 11/2010 | Biscup et al. |
| 7,850,697 B2 | 12/2010 | Ross et al. |
| 7,857,852 B2 | 12/2010 | Kuras |
| 8,096,994 B2 | 1/2012 | Phan et al. |
| 8,262,698 B2 | 9/2012 | Anderson et al. |
| 8,449,616 B2 | 5/2013 | Zimmers et al. |
| 8,642,059 B2 | 2/2014 | Trieu |
| 8,642,060 B2 | 2/2014 | Trieu |
| 8,956,412 B2 | 2/2015 | Kuras et al. |
| 9,474,847 B2 | 10/2016 | Bonutti et al. |
| 10,765,527 B2 | 9/2020 | Chin et al. |
| 2002/0049394 A1* | 4/2002 | Roy ............ A61F 2/446 623/17.11 |
| 2003/0009224 A1 | 1/2003 | Kuras |
| 2003/0208271 A1 | 11/2003 | Kuras |
| 2004/0122517 A1 | 6/2004 | Kuras |
| 2004/0186576 A1 | 9/2004 | Biscup et al. |
| 2004/0193151 A1 | 9/2004 | To et al. |
| 2005/0131543 A1 | 6/2005 | Benzel et al. |
| 2005/0131544 A1 | 6/2005 | Kuras et al. |
| 2005/0234555 A1 | 10/2005 | Sutton et al. |
| 2005/0273170 A1 | 12/2005 | Navarro et al. |
| 2006/0136061 A1 | 6/2006 | Navarro et al. |
| 2006/0142860 A1 | 6/2006 | Navarro et al. |
| 2006/0149273 A1 | 7/2006 | Ross et al. |
| 2006/0149377 A1 | 7/2006 | Navarro et al. |
| 2006/0155298 A1 | 7/2006 | Mueller et al. |
| 2006/0247773 A1* | 11/2006 | Stamp ............ A61B 5/11 623/17.11 |
| 2006/0259143 A1 | 11/2006 | Navarro et al. |
| 2006/0259146 A1 | 11/2006 | Navarro et al. |
| 2007/0225807 A1 | 9/2007 | Phan et al. |
| 2007/0233074 A1 | 10/2007 | Anderson et al. |
| 2007/0250044 A1 | 10/2007 | Trieu |
| 2007/0250045 A1 | 10/2007 | Trieu |
| 2008/0177392 A1 | 7/2008 | Williams et al. |
| 2008/0319548 A1 | 12/2008 | Kuras et al. |
| 2010/0131067 A1* | 5/2010 | Metcalf, Jr. ............ A61F 2/441 600/587 |
| 2012/0239149 A1 | 9/2012 | Zimmers et al. |
| 2014/0309585 A1 | 10/2014 | Bonutti et al. |
| 2014/0316524 A1 | 10/2014 | Zimmers et al. |
| 2015/0342746 A9 | 12/2015 | Radojicic |
| 2019/0099276 A1 | 4/2019 | Chin et al. |

OTHER PUBLICATIONS

Chinese Office Action dated Oct. 28, 2021 issued in corresponding Chinese Application No. 201880076881.1.

* cited by examiner

ARTIFICIAL DISK WITH SENSORS

CROSS REFERENCE TO RELATED APPLICATIONS

This application claims priority to U.S. patent application Ser. No. 16/148,579 entitled ARTIFICIAL DISK WITH SENSORS, filed Oct. 1, 2018, now U.S. Pat. No. 10,765,527, which claimed priority under 35 USC 119 to U.S. provisional patent Appl. No. 62/565,357, entitled ARTIFICIAL DISK WITH SENSORS, filed Sep. 29, 2017, the contents of which are incorporated herein by reference.

While not claiming priority to, the present inventive may be related to U.S. application Ser. No. 14/215,340 filed Mar. 17, 2014, which claimed priority to U.S. Provisional Appl. No. 61/792,057 filed Mar. 13, 2013, the disclosures of which are incorporated herein by reference.

While not claiming priority to, the present inventive may be related to U.S. application Ser. No. 13/047,857 filed Mar. 15, 2011, issued as U.S. Pat. No. 8,449,616, the disclosure of which is incorporated herein by reference.

While not claiming priority to, the present inventive may be related to U.S. application Ser. No. 11/821,241 filed Jun. 22, 2007, issued as U.S. Pat. No. 8,956,412, the disclosure of which is incorporated herein by reference.

While not claiming priority to, the present inventive may be related to U.S. application Ser. No. 11/294,925 filed Dec. 6, 2005, issued as U.S. Pat. No. 7,850,697, which claimed priority to U.S. Provisional Appl. No. 60/633,620 filed Dec. 6, 2004, the disclosures of which are incorporated herein by reference.

While not claiming priority to, the present inventive may be related to U.S. application Ser. No. 10/732,660 filed Dec. 10, 2003, issued as U.S. Pat. No. 7,128,761, the disclosure of which is incorporated herein by reference.

While not claiming priority to, the present inventive may be related to U.S. application Ser. No. 10/315,373 filed Dec. 10, 2002, issued as U.S. Pat. No. 7,169,181, the disclosure of which is incorporated herein by reference.

While not claiming priority to, the present inventive may be related to U.S. application Ser. No. 10/731,964 filed Dec. 10, 2003, issued as U.S. Pat. No. 7,695,517, the disclosure of which is incorporated herein by reference.

While not claiming priority to, the present inventive may be related to U.S. application Ser. No. 10/731,942 filed Dec. 10, 2003, issued as U.S. Pat. No. 7,588,600, the disclosure of which is incorporated herein by reference.

While not claiming priority to, the present inventive may be related to U.S. application Ser. No. 10/457,589 filed Jun. 9, 2003, issued as U.S. Pat. No. 7,857,852, which was a continuation of application Ser. No. 09/898,612 filed Jul. 3, 2001, issued as U.S. Pat. No. 6,607,558, the disclosures of which are incorporated herein by reference.

FIELD OF INTEREST

The present inventive concepts relate to the field of medical devices and more particularly, to the field of artificial spinal discs.

BACKGROUND

Artificial discs are known in the art for replacing a damaged spinal disc. Such discs typically include a resilient core that attempts to approximate physical qualities of a natural spinal disc existing between two vertebrae.

Some discs comprise a top plate and a bottom plate with an elastomeric layer between the two plates. The top and bottom plates connect to the vertebrae above and below the disc and the elastomeric layer approximates the functions of the natural disc that it replaces.

In some prior discs, a circuit has been embedded in the disc to passively record use data in for form of mechanical stresses experienced by the disc. The circuit can include communication means to communicate the recorded use data to an external device. Such use data can be used to determine wear and tear on the disc, which has a limited lifecycle. That is, the prosthetic replacement disc can need replacement in the future, after a certain amount of wear and tear. An ability to read and analyze the use data can help determine when the replacement of the prosthetic disc should occur.

None of the prior art discs use sensed disc conditions to actively control or influence performance of the prosthetic disc. None of the prior art discs use disc conditions actively to control or influence treatments aided by the prosthetic discs. The prior art does not teach adding a circuit to an implanted prosthetic disc, or the repair, replacement, or removal of a circuit of the prosthetic disc without removal of the prosthetic disc.

SUMMARY

In accordance with one aspect of the present disclosure, provided is a sensing artificial disc comprising: a resilient core having a top surface, a bottom surface, and at least one sidewall; at least one sensor disposed in or on the resilient core; and a wireless transmitter configured to transmit a signal representative of a sensed condition. The disc can include at least one mechanism configured to control, influence, or alter conditions of the resilient core.

In various embodiments, the at least one sensor is embedded in the resilient core.

In various embodiments, the sensing artificial comprises at least two sensors that are disposed in or on the at least one side wall of the resilient core.

In various embodiments, the at least one sensor is a strain gauge.

In various embodiments, the at least one sensor is a temperature sensor.

In various embodiments, the at least one sensor is charged wirelessly.

In various embodiments, the signal representative of the sensed condition is continuously transmitted to an external location.

In various embodiments, the signal representative of the sensed condition is stored on a storage device.

In various embodiments, the signal representative of the sensed condition is wirelessly transmitted to an external location.

In various embodiments, the sensing artificial disc further comprises a stiffening device that can be adjusted and is constructed and arranged to modify a stiffness of the sensing artificial disc.

In various embodiments, the stiffening device is configured to modify the stiffness of the sensing artificial disc in response to the sensed condition.

In various embodiments, the stiffening device is automatically adjusted in response to the sensed condition.

In various embodiments, the stiffening device is an adjustable band or strap.

In various embodiments, the stiffening device may be adjusted using an electromagnet.

In various embodiments, the sensing artificial disc further comprises an upper plate having an outer surface engageable with a first vertebra of the spinal column and an upper plate inner surface, wherein the top surface of the resilient core engages the inner surface of the upper plate.

In various embodiments, the sensing artificial disc further comprises a lower plate having an outer surface engageable with a second vertebra of the spinal column and a lower plate inner surface, wherein the bottom surface of the resilient core engages the inner surface of the lower plate.

In accordance with another aspect of the inventive concept, provided is a sensing artificial disc comprising: a resilient core having a top surface, a bottom surface, and at least one sidewall; at least one sensor disposed in or on the resilient core; a wireless transmitter configured to transmit a signal representative of a sensed condition; and a stiffening device that may be adjusted and is constructed and arranged to modify a stiffness of the sensing artificial disc.

In various embodiments, the at least one sensor is embedded in the resilient core.

In various embodiments, the sensing artificial disc comprises at least two sensors that are disposed in or on the at least one side wall of the resilient core.

In various embodiments, the at least one sensor is a strain gauge.

In various embodiments, the at least one sensor is a temperature sensor.

In various embodiments, the at least one sensor is charged wirelessly.

In various embodiments, the signal representative of the sensed condition is continuously transmitted to an external location.

In various embodiments, the signal representative of the sensed condition is stored on a storage device.

In various embodiments, the signal representative of the sensed condition is wirelessly transmitted to an external location.

In various embodiments, the stiffening device modifies the stiffness of the sensing artificial disc in response to the sensed condition.

In various embodiments, the stiffening device is automatically adjusted in response to the sensed condition.

In various embodiments, the stiffening device is an adjustable band or strap.

In various embodiments, the stiffening device may be adjusted using an electromagnet.

In various embodiments, the sensing artificial disc further comprises an upper plate having an outer surface engageable with a first vertebra of the spinal column and an upper plate inner surface, wherein the top surface of the resilient core engages the inner surface of the upper plate.

In various embodiments, the sensing artificial disc further comprises a lower plate having an outer surface engageable with a second vertebra of the spinal column and a lower plate inner surface, wherein the bottom surface of the resilient core engages the inner surface of the lower plate.

In accordance with another aspect of the inventive concept, provided is a method of measuring a condition of a sensing artificial disc comprising: providing a resilient core having a top surface, a bottom surface, and at least one sidewall; providing at least one sensor disposed in or on the resilient core; sensing a condition of the resilient core using the at least one sensor; and transmitting a signal representative of the sensed condition to an external location using a wireless transmitter.

In various embodiments, the at least one sensor is embedded in the resilient core.

In various embodiments, the sensing artificial disc comprises at least two sensors that are disposed in or on the at least one side wall of the resilient core.

In various embodiments, the at least one sensor is a strain gauge.

In various embodiments, the at least one sensor is a temperature sensor.

In various embodiments, the at least one sensor is charged wirelessly.

In various embodiments, the signal representative of the sensed condition is continuously transmitted to an external location.

In various embodiments, the signal representative of the sensed condition is stored on a storage device.

In various embodiments, the signal representative of the sensed condition is wirelessly transmitted to an external location.

In various embodiments, the sensing artificial disc further comprises a stiffening device that can be adjusted and is constructed and arranged to modify the stiffness of the sensing artificial disc.

In various embodiments, the stiffening device modifies the stiffness of the sensing artificial disc in response to the sensed condition.

In various embodiments, the stiffening device is automatically adjusted in response to the sensed condition.

In various embodiments, the stiffening device is an adjustable band or strap.

In various embodiments, the stiffening device may be adjusted using an electromagnet.

In various embodiments, the sensing artificial disc further comprises an upper plate having an outer surface engageable with a first vertebra of the spinal column and an upper plate inner surface, wherein the top surface of the resilient core engages the inner surface of the upper plate.

In various embodiments, sensing artificial disc further comprises a lower plate having an outer surface engageable with a second vertebra of the spinal column and a lower plate inner surface, wherein the bottom surface of the resilient core engages the inner surface of the lower plate.

In accordance with another aspect of the inventive concepts, provided is a prosthetic disc comprising a resilient core and a medication disposed within the resilient core, wherein the resilient core is configured to release the medication in response to at least one condition.

In various embodiments, at least some of the resilient core includes a semipermeable material configured to release the medication external to the resilient core.

In various embodiments, the medication is distributed throughout the resilient core and released over time.

In various embodiments, the medication is maintained in at least one reservoir within the semipermeable core.

In various embodiments, the at least one reservoir is refillable.

In various embodiments, the at least one reservoir is a plurality of reservoirs.

In various embodiments, the at least one reservoir is a single reservoir.

In various embodiments, the medication is time-released and the condition is the passage of time.

In various embodiments, the condition is pressure applied to the resilient core.

In various embodiments, the disc includes a plurality of medications.

In various embodiments, the disc includes a plurality of medications.

In various embodiments, the disc further comprises at least one sensor disposed in or on the resilient core and a wireless transmitter configured to transmit a signal representative of a sensed condition.

In various embodiments, the at least one sensor includes a medication sensor configured to sense a level of the medication.

In various embodiments, the wireless transmitter transmits a signal indicating that the medication level is below a threshold level.

In various embodiments, the disc further comprises at least one mechanism configured to control, influence, or alter conditions of the resilient core.

In various embodiments, the at least one mechanism is configured to cause the medication to be released external to the resilient core in response to a sensed condition.

In accordance with another aspect of the inventive concepts, provided is a prosthetic disc comprising a resilient core having a top surface, a bottom surface, and at least one sidewall, at least one sensor disposed in or on the resilient core, a wireless transmitter configured to transmit a signal representative of a sensed condition, and at least one mechanism configured to control, influence, or alter conditions of the resilient core.

In various embodiments, the at least one sensor is embedded in the resilient core.

In various embodiments, the prosthetic disc comprises at least two sensors that are disposed in or on the at least one side wall of the resilient core.

In various embodiments, the at least one sensor is a strain gauge.

In various embodiments, the at least one sensor is a temperature sensor.

In various embodiments, the at least one sensor is charged wirelessly.

In various embodiments, the signal representative of the sensed condition is continuously transmitted to an external location.

In various embodiments, the signal representative of the sensed condition is stored in a storage device.

In various embodiments, the signal representative of the sensed condition is wirelessly transmitted to an external device.

In various embodiments, the at least one mechanism comprises a stiffening device that is adjustable to modify a stiffness of the resilient core.

In various embodiments, the stiffening device includes at least one heating element configured to raise a temperature of at least one region of the resilient core.

In various embodiments, the stiffening device includes a plurality of heating elements configured to raise a temperature of a plurality of different regions of the resilient core.

In various embodiments, the stiffening device includes at least one piezo element.

In various embodiments, the stiffening device is configured to modify the stiffness of the resilient core in response to the sensed condition.

In various embodiments, the stiffening device is automatically adjustable in response to the sensed condition.

In various embodiments, the stiffening device is an adjustable band or strap.

In various embodiments, the stiffening device is adjustable using an electromagnet.

In various embodiments, the prosthetic disc further comprises a medication disposed within the resilient core, wherein the resilient core is configured to release the medication in response to at least one condition.

In various embodiments, the resilient core includes a semipermeable material configured to release the medication external to the resilient core.

In various embodiments, the medication is maintained in at least one reservoir within the resilient core.

In various embodiments, the at least one reservoir is refillable.

In various embodiments, the disc further comprises a medication sensor configured to sense a level of the medication in the reservoir and the wireless transmitter is configured to transmit a signal indicating a level of the medication in the reservoir.

In accordance with another aspect of the inventive concepts, provided is a method of adjusting the stiffness of prosthetic spinal disc, comprising providing a resilient core having a top surface, a bottom surface, and at least one sidewall, providing at least one sensor disposed in or on the resilient core, sensing a condition of the resilient core using the at least one sensor, and adjusting a stiffness of the resilient core in response to the sensed condition.

In accordance with another aspect of the inventive concepts, provided is a prosthetic disc as shown and described.

In accordance with another aspect of the inventive concepts, provided is a method of adding a sensing circuit or its elements to an implanted prosthetic disc as shown and described.

In accordance with another aspect of the inventive concepts, provided is a method of removing a sensing circuit or its elements from an implanted prosthetic disc as shown and described.

In accordance with another aspect of the inventive concepts, provided is a method of replacing and/or repairing a sensing circuit or its elements of an implanted prosthetic disc as shown and described.

In accordance with another aspect of the inventive concepts, provided is a method of providing an artificial sensing disc as shown and described.

BRIEF DESCRIPTION OF THE DRAWINGS

The present invention will become more apparent in view of the attached drawings and accompanying detailed description. The embodiments depicted therein are provided by way of example, not by way of limitation, wherein like reference numerals refer to the same or similar elements. The drawings are not necessarily to scale, emphasis instead being placed upon illustrating aspects of the invention. In the drawings.

DETAILED DESCRIPTION OF PREFERRED EMBODIMENTS

Figure 1:
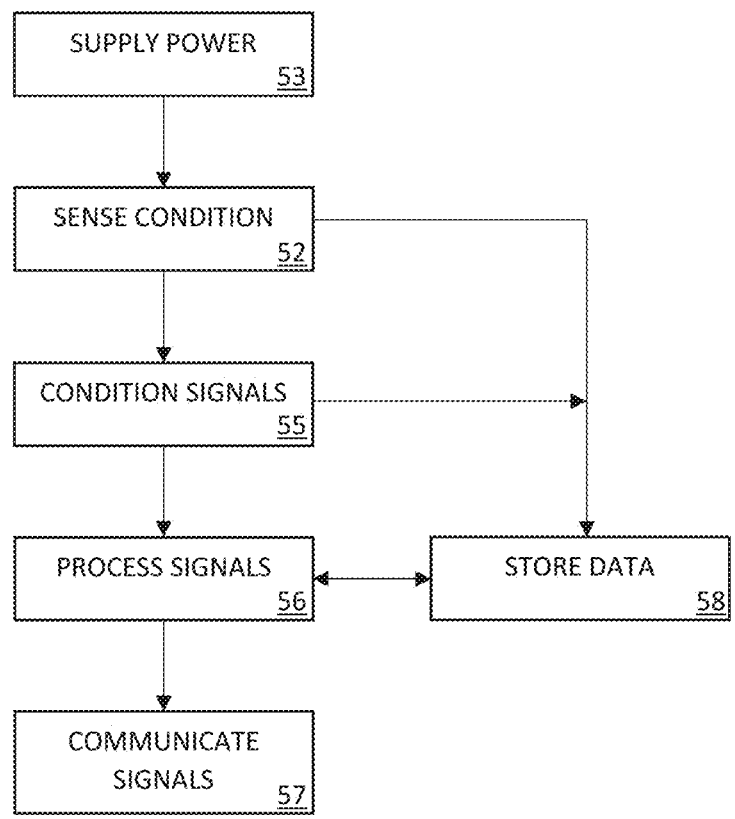
FIG. 1 is a flowchart of an embodiment of a method of monitoring conditions and/or within an artificial spinal disc, in accordance with aspects of the inventive concept.

Various aspects of the inventive concepts will be described more fully hereinafter with reference to the accompanying drawings, in which some exemplary embodiments are shown. The present inventive concept may, however, be embodied in many different forms and should not be construed as limited to the exemplary embodiments set forth herein.

It will be understood that, although the terms first, second, etc. are used herein to describe various elements, these elements should not be limited by these terms. These terms are used to distinguish one element from another, but not to imply a required sequence of elements. For example, a first element can be termed a second element, and, similarly, a second element can be termed a first element, without departing from the scope of the present invention. As used herein, the term "and/or" includes any and all combinations of one or more of the associated listed items.

It will be understood that when an element is referred to as being "on" or "connected" or "coupled" to another element, it can be directly on or connected or coupled to the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, steps, operations, elements, and/or components, but do not preclude the presence or addition of one or more other features, steps, operations, elements, components, and/or groups thereof.

Spatially relative terms, such as "beneath," "below," "lower," "above," "upper" and the like may be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in the figures is turned over, elements described as "below" and/or "beneath" other elements or features would then be oriented "above" the other elements or features. The device may be otherwise oriented (e.g., rotated 90 degrees or at other orientations) and the spatially relative descriptors used herein interpreted accordingly.

Exemplary embodiments are described herein with reference to cross-sectional illustrations that are schematic illustrations of idealized exemplary embodiments (and intermediate structures). As such, variations from the shapes of the illustrations as a result, for example, of manufacturing techniques and/or tolerances, are to be expected. Thus, exemplary embodiments should not be construed as limited to the particular shapes of regions illustrated herein but are to include deviations in shapes that result, for example, from manufacturing.

To the extent that functional features, operations, and/or steps are described herein, or otherwise understood to be included within various embodiments of the inventive concept, such functional features, operations, and/or steps can be embodied in functional blocks, units, modules, operations and/or methods. And to the extent that such functional blocks, units, modules, operations and/or methods include computer program code, such computer program code can be stored in a computer readable medium, e.g., such as non-transitory memory and media, that is executable by at least one computer processor.

This disclosure describes embodiments of the present inventive concepts in which a sensing artificial disc includes at least one sensor.

The sensing artificial disc can include one or more features of an apparatus for replacing a damaged spinal disc, for example, as described in U.S. patent application Ser. No. 13/047,857, filed Mar. 15, 2011, the contents being incorporated by reference in their entirety.

The at least one sensor can be a sensor constructed and arranged to generate a signal representative of a sensed condition. Sensed conditions can include compression, extension, strain, temperature, torsion, sheer, shock, acceleration and/or another parameter.

The at least one sensor may be embedded in the sensing artificial disc or may be positioned on an exterior surface of the sensing artificial disc.

FIG. 1 is a block diagram of an embodiment of a method of sensing conditions of a resilient core implemented by the sensing artificial disc 100 of the present inventive concepts.

The sensing artificial disc includes at least one sensor 2, which is powered by at least one power source 3 in step 53. In step 52, the at least one sensor 2 senses at least one condition. The at least one sensor 2, e.g., a strain gauge and/or temperature sensor, may be included within and/or on a resilient core 10 and powered by a battery or other such power device 3. The power device 3 may be embedded in the sensing artificial disc 100 or may be positioned on an exterior surface of the sensing artificial disc 100 or may be positioned at a different location. As an example, the power device 3 may be based on the architecture of "implantable cardioverter-defibrillators," which are similar to pacemakers, and currently last for 6-10 years.

In some embodiments, the power device 3 may be charged wirelessly. An induction charger 4 may be coupled to the power device 3 for such purposes. The induction charger 4 may be embedded in the sensing artificial disc 100 or may be positioned on an exterior surface of the sensing artificial disc 100 or may be positioned at a different location.

In some embodiments, the power device 3 may be charged by converting motion energy into electrical energy. Piezoelectric structures may be used to harvest energy from motion, as an example.

A signal representative of a sensed condition that is generated by one or more sensors 2 can be sent to a signal conditioner 5, in step 55. Such signals could also be stored in a memory 8, in step 58. The signal conditioner 5 may be embedded in the sensing artificial disc 100, e.g., with one or more sensors and one or more data storage devices, or may be positioned on an exterior surface of the sensing artificial disc 100 or may be positioned at a different location. The signal conditioner 5 may prepare the signal representation from the one or more sensors 2 for further processing in step 56, e.g., by at least one processor 6. The condition signals can also be stored in the memory 8, in step 58. The processor 6 could receive or access the conditioned signals from the memory 8, the signal conditioner 5, and/or the sensors 2. In some embodiments signal conditioning and a signal conditioner may not be included.

In step 56, the signal representation can be sent to the processor 6, such as a microprocessor. The processor 6 may be embedded in the sensing artificial disc 100 or can be positioned on an exterior surface of the sensing artificial disc 100 or may be positioned at a different location.

In step 57, a wireless transmitter 7 can be configured to transmit the signal representative of the sensed condition or a signal determined based on the sensed condition to an external location and device, e.g., outside the body. In some embodiments, the wireless transmitter 7 can be an antenna. The signal may be transmitted continuously or the signal may be stored on a storage device 8, or both. That is, the signal that is stored in memory storage device 8 can be transmitted at a later time, such as using passive RFID. For example, the storage device 8 can be a semiconductor memory. In step 57, the sensing artificial disc 100 may be configured to communicate the signal using an active or a passive RFID system, in various embodiments.

The signal can be transmitted to an external location and/or device with electrical connections or wirelessly. If the signal representation is transmitted wirelessly, it can be transmitted by the wireless transmitter 7. The wireless transmitter 7 may be embedded in the sensing artificial disc 100 or may be positioned on an exterior surface of the sensing artificial disc 100 or may be positioned at a different location.

The signal may be transmitted from the wireless transmitter to an external location and/or device using standard network protocols, for example, it could be transmitted via Bluetooth, Bluetooth LE, RFID, ANT+, NFC, LoRaWAN, etc.

Figure 2:
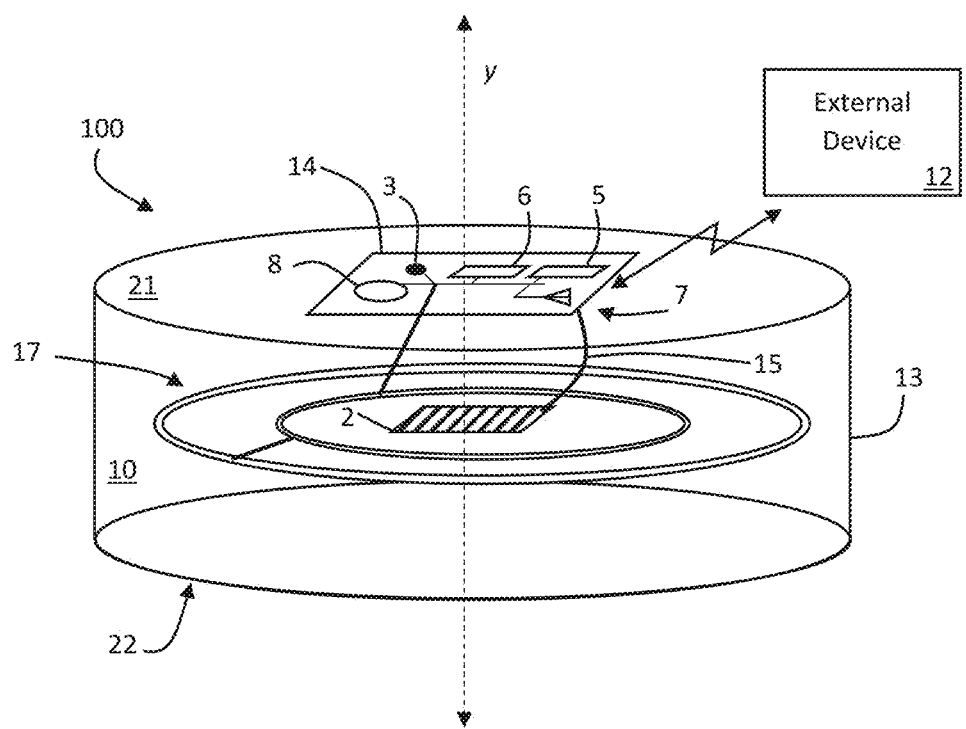
FIG. 2 provides a perspective view of an embodiment of a sensing artificial disc in accordance with aspects of the inventive concept.

FIG. 2 shows a perspective view of an embodiment of a sensing artificial disc 100 in accordance with aspects of the inventive concept. The sensing artificial disc 100 includes a resilient core 10 and at least one sensor 2 arranged to sense at least one condition associated with the resilient core 10. Such conditions can include changes in load, temperature, torque, and so on. The at least one sensor 2 can be disposed on a surface of the resilient core, within or internal to the resilient core (as is shown), and/or some combination thereof, in various embodiments. In FIG. 2, a single sensor is shown as an example.

The resilient core 10 can be any resilient core used for artificial discs presently or hereafter known in the art, such as those made from an elastomeric material. The resilient core 10 can have a size and a shape that matches, mimics, or approximates that of the disc being replaced, such as a natural spinal disc. As examples, the resilient core 10 can be made from a polymeric material, a urethane-silicon blend, or other biocompatible shape memory materials, or combinations thereof. The resilient core 10 could be made from a single material or from a plurality of different materials.

The resilient core 10 can have a top surface 21 spaced apart from a bottom surface 22 with at least one side or sidewall 13 connecting the top and bottom surfaces. The top surface 21 and the bottom surface 22 can be oriented in parallel, in some embodiments. The top surface 21, bottom surface 22, and at least one sidewall 13 can define an internal volume of the resilient core 10. The one or more sensors 2 can be disposed within the internal volume of the resilient core 10, e.g., as shown in FIG. 2.

The sensing artificial disc 100 can further comprise sensing electronics 14 configured to exchange data, information, signals, and/or instructions with the at least one sensor 2. Such data, information, signals, and/or instructions can be exchanged between the at least one sensor 2 and the sensing electronics 14 via at least one communication path 15, which can be wired, wireless, or some combination thereof.

The sensing electronics 14 can comprise at least one power source 3, at least one processor (or microprocessor) 6, at least one storage device 8, and/or a wireless transmitter 7. The processor 6 is configured to process data, information, and/or signals from the one or more sensors 2. Some or all of the sensing electronics 14 can be located in the resilient core 10, on a surface or side of the resilient core 10, external to the resilient core 10, and/or external to the patient's body. In the embodiment of FIG. 2, processor 6 is located on a surface of resilient core 10, as part of the sensing electronics 14.

In FIG. 2, sensor 2 and processor 6 are both disposed in a center of the resilient core 10, on a central axis "y." But this need not be the case in all embodiments. As one example, in some embodiments one or more sensors 2 can be located on central axis y, while the sensing electronics 14, or portions thereof, are located elsewhere in, on, and/or outside the resilient core 10. As another example, in some embodiments, sensing electronics 14 can be located on central axis y, while one or more sensors 2, or portions thereof, is located elsewhere in and/or on the resilient core 10. As another example, in some embodiments neither the sensors 2 nor the sensing electronics 14 is located on the central axis y.

In various embodiments, the one or more sensors 2 may be configured to transmit data, information, and/or signals indicative of a sensed condition external to the sensing artificial disc 100. In some embodiments, the sensing electronics 14 can include at least one wireless transmitter 7 configured to accomplish such wireless transmissions to an external device 12. Such external device can include a wireless receiver, transmitter, or transceiver. The external device 12 can be configured to wirelessly interrogate the electronics 14 and/or sensor 2 to transmit data. For example, the electronics 14 can transmit stored data from memory 8, such as a history of sensed data or a current sensed condition (e.g., strain, torque, or temperature). In some embodiments, the external device 12 can communicate executable instructions to processor 6. In some embodiments, the external device 12 can communicate programming updates to electronics 14, which are executable by processor 6 to update, for example, software or settings of the electronics 14.

In some embodiments, the external device 12 could be a mobile device (e.g., smartphone) of the person within which the prosthetic disc was implanted. The mobile device 12 could include an application that alerts the user and/or the user's healthcare provider to the sensed condition.

In some embodiments, the stiffness of the sensing artificial disc 100 can be modifiable in response to at least one stimulus, force, and/or condition. The stimulus can be provided as signals generated in response to the sensors 2 sensing a condition or a state or a change in condition or a change in state, which can be referred to as sensor signals. In such cases, the sensing artificial disc 100 can include one or more electrical, mechanical, electromechanical and/or inductive devices that responds to such sensor signals, referred to as stiffening devices. In some embodiments, the stiffening device is automatically adjusted in response to the sensed condition.

For example, the sensing artificial disc 100 can also include mechanisms 17 to control, influence, or alter conditions of the resilient core 10. In such embodiments, the electronics 14 activates the mechanisms 17 in response to signals from the sensors 2. In various embodiments, activation of the mechanisms provides some ameliorative or therapeutic effect.

In an embodiment of FIG. 2, a heating element 17 is used to heat the resilient core 10, which can increase the softness and/or pliability of the resilient core, or portions thereof. For example, changing or influencing the softness and/or pliability of the resilient core 10 can provide benefits to the living being when the sensing artificial disc 100 experiences certain mechanical stresses. The heating element in this embodiment includes a plurality of concentric rings disposed within the resilient core 10. The rings are connected to the sensing electronics 14, and are responsive to control signals from the sensing electronics to raise and lower temperature within the resilient core 10. The rings can be commonly controlled or individually controlled. If individually controlled, each ring could be turned on and off independently, and the rings could be set to different temperatures. In some embodiments, different portions of a ring could be independently controlled. In such cases, a specific portion of the resilient core could be heated independently by heating different portions of one or more rings. Therefore, different regions of the resilient core can have different temperatures and, as result, different degrees of stiffness. While rings are shown in this embodiment, heating elements could take other forms in other embodiments, e.g., a coil or various forms of wires.

Figure 3A:
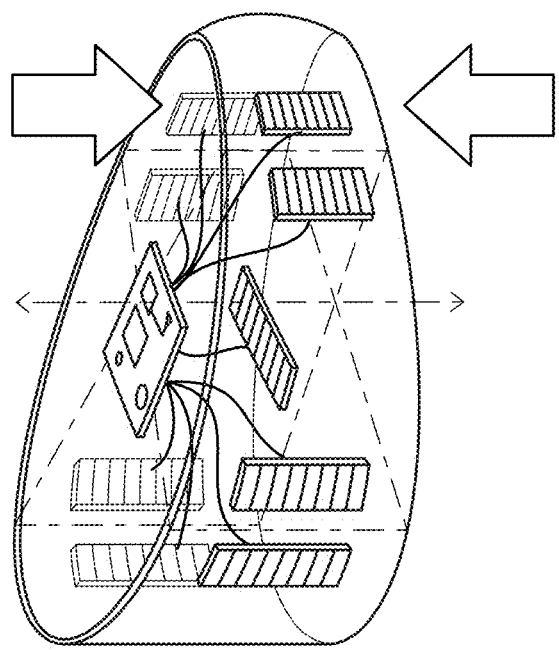
FIG. 3A provides a perspective view of another embodiment of a sensing artificial disc in accordance with aspects of the inventive concept.
Figure 3:
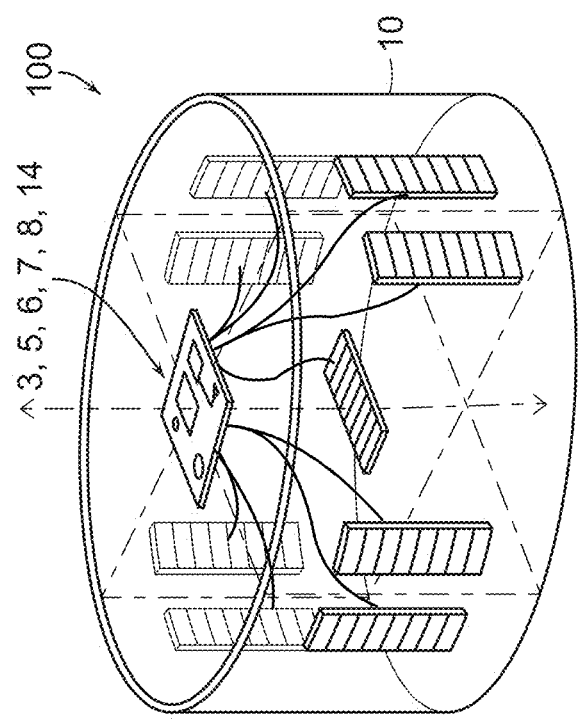
FIG. 3 provides a perspective view of another embodiment of a sensing artificial disc in accordance with aspects of the inventive concept.

FIG. 3 provides a perspective view of another embodiment of a sensing artificial disc 100, in accordance with aspects of the inventive concept.

In FIG. 3, the processor 6 is coupled to a plurality of sensors 2. The sensors 2 are located at different positions within and on the sensing artificial disc. In this embodiment, the sensors 2 can be configured to measure the compression and the extension of the resilient core 10 of the sensing artificial disc 100. With multiple sensors, the sensing artificial disc 100 can measure the direction of extension and/or the compression.

The processor 6, the wireless transmitter 7, the storage device 8, and the power device 3 can be mounted on a printed circuit board, for example, as the sensing electronics 14. The printed circuit board can be disposed within or mounted to the sensing artificial disc 100. In this embodiment, a sensor 2 is disposed in the center of the resilient core 10, as in FIG. 2, with a plurality of sensors 2 dispersed around a perimeter of the sensing artificial disc 100, proximate to, within, or on the sidewall 13 of the sensing artificial disc 100.

In FIG. 3, the sensors are shown in pairs, e.g., as paired strain gauges. In other embodiments, the sensors 2 can be positioned such that they are not in pairs.

In FIG. 3, the sensors on the side 13 are vertically oriented and the sensor in the middle is horizontally oriented. In other embodiments, the sensors 2 can be oriented in different configurations. The multiple sensors and/or sensor pairs can be configured to communicate with the sensing electronics 14, e.g., processor 6, wireless transmitter 7, and storage device 8, via a wired and/or wireless connection.

FIG. 3A provides a perspective view of the sensing artificial disc 100 of FIG. 3 partially compressed on one side in response to forces, indicated by two arrows. The sensors 2 are positioned around the outer edge of the resilient core 10, which allows the sensing artificial disc 100 to measure not only a magnitude of compression, but also a direction of the compression. In this embodiment, therefore, the sensing artificial disc 100 is configured to sense a plurality of different conditions of the resilient core 10 based on forces exerted thereon.

Like the embodiment of FIG. 2, the sensing artificial disc 100 of FIG. 3 can include one or more mechanisms 17 configured to control, influence, or alter conditions of the resilient core 10. In such embodiments, the electronics 14 activates the mechanisms 17, e.g., one or more heating elements, in response to signals from the sensors 2. Using different sensors 2 and different mechanisms 17, e.g., heating elements, the conditions in different regions of the resilient core 10 can be different. For example, some regions of the resilient core 10 can be selectively heated, so that different regions of the resilient core 10 have different temperatures and, as a result, different degrees of stiffness. In various embodiments, activation of the mechanisms provides some ameliorative or therapeutic effect.

Figure 4:
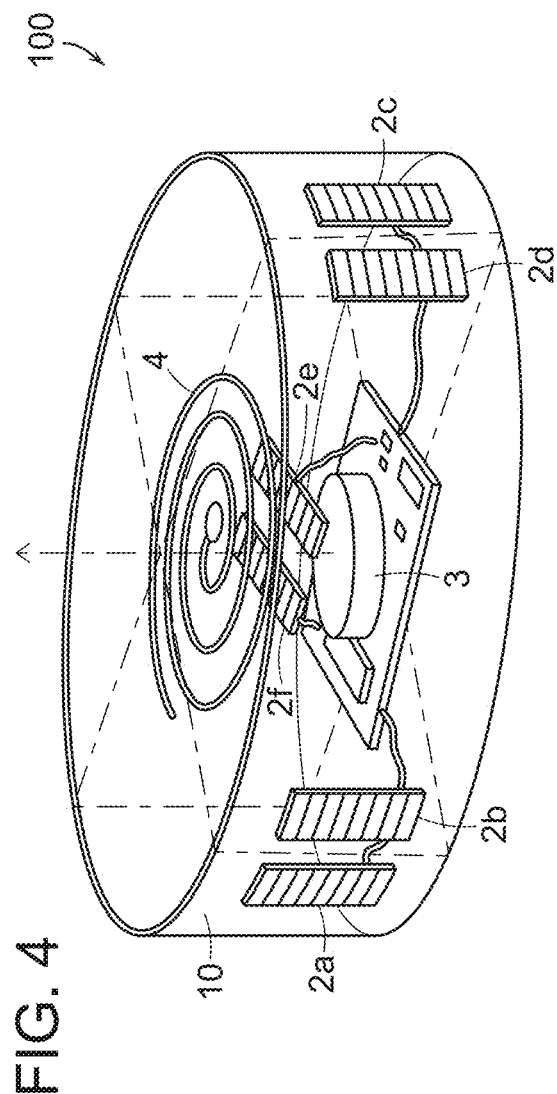
FIG. 4 provides a perspective view of another embodiment of a sensing artificial disc in accordance with aspects of the inventive concept.

FIG. 4 provides a perspective view of another embodiment of a sensing artificial disc 100 in accordance with aspects of the inventive concept.

In the embodiment of FIG. 4, a pair of sensors 2 is horizontally oriented in a middle or central portion of the resilient core 10. The sensing electronics 14 includes the power device 3, processor 6, storage device 8, wireless transmitter 7, and induction charger 4, which are embedded in the sensing artificial disc 100, in this embodiment. The induction charger 4 provides a mechanism for charging the power device 3. In this embodiment, a printed circuit board having the processor 6, wireless transmitter 7 and memory 8 is disposed below the sensor pair and the induction charger 4 is disposed above the sensor pair, in a spaced stacked arrangement with respect to the center axis y. The sensing electronics 14 can be connected by one or more wires 11, e.g., within the resilient core 10.

Also in FIG. 4, a plurality of sensors 2a-f are vertically oriented around a periphery of the resilient core 10, with the centrally, horizontally oriented pair of sensors disposed therebetween. In other embodiments, the sensors 2 can be arranged differently.

The vertically oriented sensors 2a-f are positioned in pairs at different locations on or within the sides of the resilient core 10, either on outer surfaces of the resilient core 10 or inside the resilient core 10. In this embodiment, there are four pairs of vertically oriented sensors, which can all be 90 degrees apart with respect to the central axis y. One or more of the vertically oriented sensors, e.g., sensor 2c, is embedded in a sensor holder 22 at the periphery of the side of the resilient core 10. The other vertically oriented sensors could be similarly embedded in the sensor holder 22 on the side of the resilient core. In other embodiments, the sensors 2 can be arranged differently.

Figure 5:
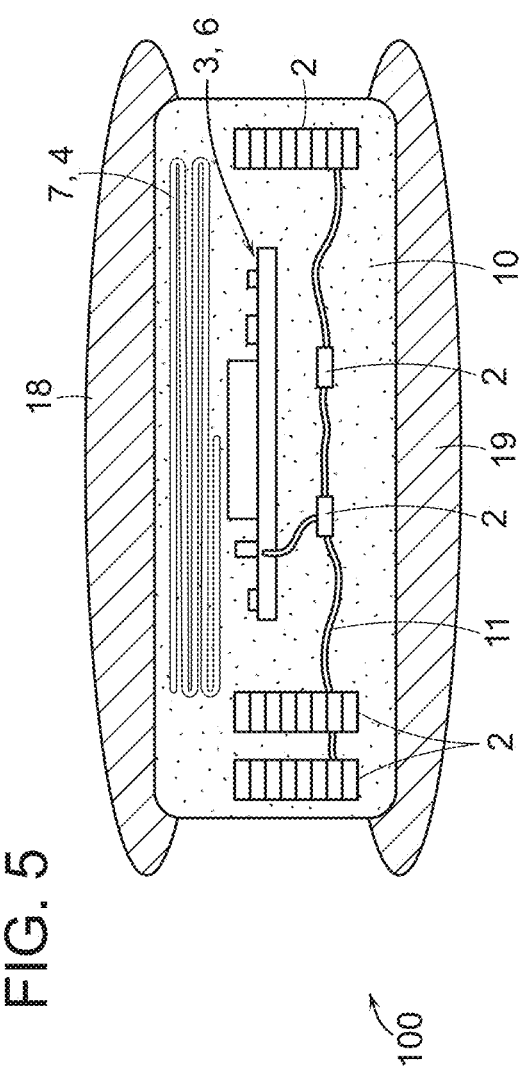
FIG. 5 provides a side view of an embodiment of a sensing artificial disc 100', in accordance with aspects of the inventive concept.

FIG. 5 shows a side view of an embodiment of a sensing artificial disc 100, in accordance with aspects of the inventive concept. In the embodiment of FIG. 5, the sensing artificial disc 100 includes an upper plate 18 coupled to the top surface 21 of the resilient core 10 and a lower plate 19 coupled to the bottom surface 22 of the resilient core 10. The upper and/or lower plates 18, 19, when included, could be configured to engage two vertebrae between which the sensing artificial disc 100 is ultimately disposed within a patient.

In the embodiment of FIG. 5, a plurality of sensors 2 are positioned at different locations on or near the sides of the resilient core 10, as well as inside the resilient core 10. The power device 3, processor 6, storage device 8, wireless transmitter 7, and induction charger 4 are embedded within the resilient core 10 of the sensing artificial disc 100, in this embodiment.

In FIG. 5, a pair of sensors 2 is horizontally oriented in a middle or central portion of the resilient core 10 and a plurality of pairs of vertically oriented sensors is disposed around a periphery of the resilient core 10. In this embodiment, a printed circuit board having the processor 6, wireless transmitter 7 and storage device 8 is disposed above the sensor pair and the induction charger 4 is disposed above the printed circuit board, in a spaced stacked arrangement relative to the vertical center axis y. The electronics can be connected by one or more wires 11, e.g., within the resilient core 10, as in FIG. 4.

The stiffness of the sensing artificial disc 100 can be modifiable in response to at least one stimulus, force, and/or condition. The stimulus can be provided as signals generated in response to the sensors 2 sensing a condition or a state or a change in condition or a change in state, which can be referred to as sensor signals. In such cases, the sensing artificial disc 100 can include one or more electrical, mechanical, electromechanical and/or inductive devices that responds to such sensor signals, referred to as stiffening devices. In some embodiments, the stiffening device is automatically adjusted in response to the sensed condition.

Like the embodiment of FIG. 2, the sensing artificial disc 100 of FIG. 4 can include one or more mechanisms 17 configured to control, influence, or alter conditions of the resilient core 10. In such embodiments, the electronics 14 activates the mechanisms 17, e.g., one or more heating elements, in response to signals from the sensors 2. In various embodiments, activation of the mechanisms provides some ameliorative or therapeutic effect.

Figure 6:
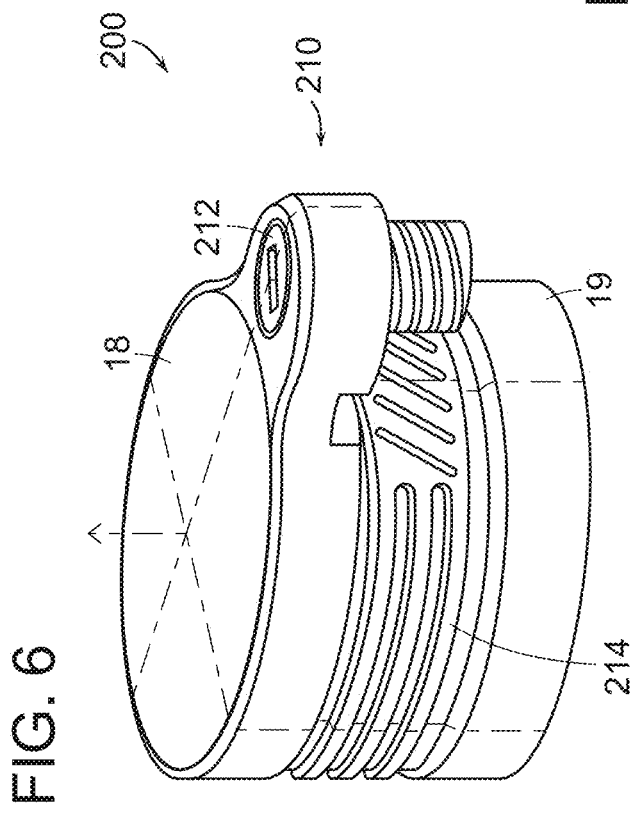
FIG. 6 provides a perspective view of another embodiment of a sensing artificial disc in accordance with aspects of the inventive concept.

FIG. 6 shows a perspective view of a sensing artificial disc 200 with a clamp 210 that allows the stiffness of the resilient core 10 to be modified, as an embodiment of a stiffening device. The sensing artificial disc 200 can include sensors 2 and sensing electronics 14 discussed above, as well as one or more mechanisms 17 configured to control, influence, or alter conditions of the resilient core 10. In the embodiment of FIG. 6, clamp 210 is an embodiment of a mechanisms 17 configured to control, influence, or alter conditions of the resilient core 10 that is not a heating element, but still may be responsive to a condition sensed by the sensors 2.

Different types of clamps can be used, for example, in some embodiments, the stiffness may be modified by a hose clamp or a band clamp. In this embodiment, the clamp 210 is disposed around the disc-shaped resilient core 10, such that it can increase and/or decrease pressure to the sides of the resilient core by tightening and losing the clamp 210, respectively.

In FIG. 6, top and bottom plates 18, 19 are included with the resilient core 10 disposed there between, see, e.g., FIG. 4. A channel is formed between the top and bottom plates that constrains vertical movement of the clamp 210. A channel could also be formed in the sides of the resilient core for the same purposes, particularly if the top and bottom plates were not included.

In various embodiments, the clamp 210 may be composed of different materials, for example nitinol (NiTi) or fabric or some other material. In this embodiment, the clamp 210 includes a lead screw 212 that engages a band 214 to tighten or loosen the band around the resilient core 10, thereby controlling the durometer of the resilient core 10.

In one embodiment, the clamp 210 can be tightened using an external electromagnet to turn the lead screw 212. In yet another embodiment, the induction coil can be used to generate a magnetic field that constrains and loosens the clamp band in response to one or more sensor signals, e.g., by causing the lead screw 212 to rotate.

Figure 7:
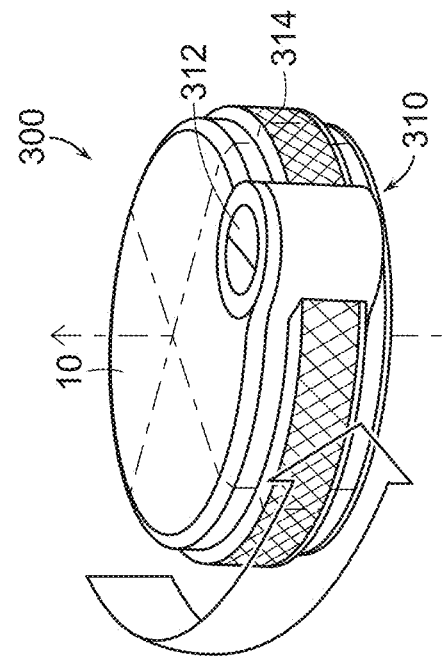
FIG. 7 provides a perspective view of another embodiment of a sensing artificial disc in accordance with aspects of the inventive concept.

FIG. 7 provides a perspective view of another embodiment of a sensing artificial disc 300 having a stiffening device 310, in accordance with aspects of the inventive concept. The sensing artificial disc 300 can include sensors 2 and sensing electronics 14 discussed above, as well as one or more mechanisms 17 configured to control, influence, or alter conditions of the resilient core 10. In this embodiment, the mechanisms 17 includes or takes the form of a stiffening device 310 is used to cause durometer changes to the resilient core 10. As in the embodiment of FIG. 6, the sensing artificial disc has a stiffening device 310 that includes a band or strap 314. The stiffening device also includes a rotatable screw 312 that can be controlled electromagnetically so that it can modulate the stiffness of the strap 314.

In one embodiment, the clamp 310 can be tightened using an external electromagnet to turn the clamp band 314. In yet another embodiment, the induction coil 4 can be used to generate a magnetic field that constrains and loosens the clamp band in response to one or more sensor signals from sensors 2, e.g., by causing the electromagnet 312 to rotate the durometer modulation is achieved through tightening or loosening of clamp band 314.

Figure 8:
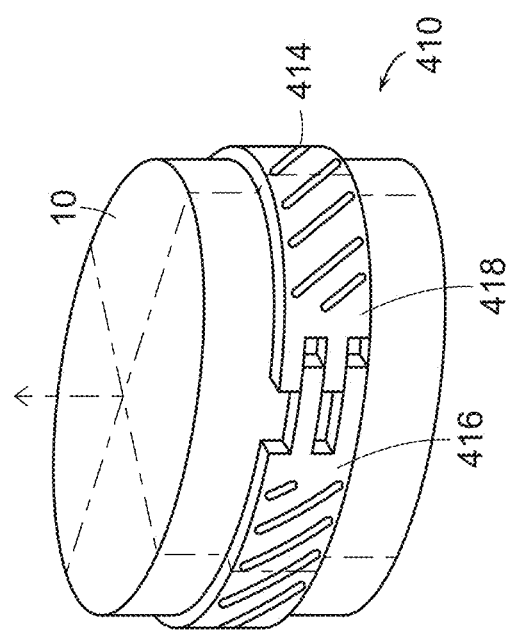
FIG. 8 provides a perspective view of another embodiment of a sensing artificial disc in accordance with aspects of the inventive concept.

FIG. 8 provides a perspective view of another embodiment of a sensing artificial disc 400 having a stiffening device 410, in accordance with aspects of the inventive concept. The sensing artificial disc 400 can include sensors 2 and sensing electronics 14 discussed above, as well as one or more mechanisms 17 configured to control, influence, or alter conditions of the resilient core 10. In this embodiment, the mechanisms 17 includes or takes the form of a stiffening device 410 having a band 414 with a first end 416 that abuts and mates with a second end 418. The band 414 is disposed about the resilient core 10, in particular engaging sides of the resilient core 10. In this embodiment, the first and second ends of the band have a tongue and groove form, where the tongues of one end are partially or fully received by the corresponding grooves of the other end. The band 414 can be formed to be biased in a closed state, e.g., where it has its minimum diameter. The band can be expanded into an open state as compression and/or deformation of the disc causes the disc to change shape, e.g., bulge in at least one direction. In attempting to return to its closed state, the band 414 can impart a compressive force on the sides of the resilient core 10, e.g., toward the vertical central axis y. Therefore, the band can be formed from a memory material in some embodiments that resists at least lateral deformation of the resilient core 10.

In some embodiments, the band can be composed of a single continuous loop, made of shape-memory material. These embodiments can include, but are not limited to, a woven NiTi band, a magnetic shape-memory material, or a magnetic shape-memory alloy. In these embodiments, the band can be modulated without tightening the lead screw 212 (FIG. 6) or the rotatable screw 312 (FIG. 7). In some embodiments, the band can be adjusted in response to a change in temperature or in response to a change in the magnetic field.

In various embodiments, the disc 200, 300, and/or 400 can be provided without the sensors and sensing electronics, as discs with mechanical mechanisms useful for adjusting the stiffness of the resilient core.

Figure 9A:
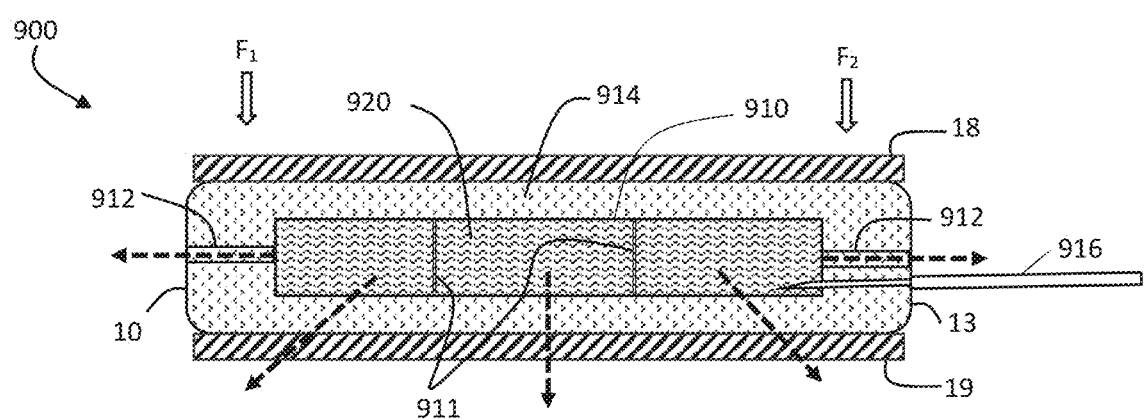
FIG. 9A is a side view of a prosthetic disc having an therapeutic delivery system in accordance with aspects of the inventive concept.

FIG. 9A is a side view of an embodiment of a prosthetic disc 900 having a therapeutic delivery system. In this embodiment, within the resilient core 10 is disposed a quantity of medication 920. The medication 920 can be provided within a bladder, compartment, or reservoir 910 within the resilient core 10. The medication can be any of a variety of forms for medication developed to treat any of a variety of diseases and/or conditions, e.g., cancer, diabetes, inflammation, heart disease, and so on. For example, the medication can be an anti-inflammatory, a blood thinner, insulin, a cancer treatment drug, and so forth.

In some embodiments, the resilient core 10 can include a semipermeable material that enables release or seepage of the medication 910 through the resilient core 10 to the body. In some embodiments, the resilient core 10 can include one or more channels 912 connecting the reservoir to an external surface of the resilient core, such as side 13. The channels are configured to provide a path for the medication 920 to be released from the reservoir 910 to the body, external to the disc 900.

In some embodiments, release of the medication can be timed released. In some embodiments, release of the medication can be in response to forces ($F_1$, $F_2$) exerted on the disc 900, such as forces applied to upper plate 18 and/or lower plate 19 through body movements. In such cases, the forces can apply a compressive force on the reservoir that forces medication 920 out of the reservoir 910 and external to the resilient core 10, e.g., through the semipermeable material 914 of the resilient core 10 and/or the channels 912.

In FIG. 9A, a single reservoir 910 can be a single reservoir containing a single medication 920. In other embodiments, there may be a plurality of reservoirs within resilient core 10. In other embodiments, there may be a plurality of medications provided in one or more reservoirs within resilient core 10. For instance, reservoir 920 could include a plurality of compartments containing different medications. For example, in some embodiments, reservoir 910 could optionally include one or more dividers 911 that create sub-reservoirs within reservoir 910. Different compartments could hold different medications 920.

The reservoir 910 can be refillable, in some embodiments. In such cases, a medication delivery apparatus 916 can be used to add medication to the reservoir. The medication delivery apparatus 916 can take the form of a medical needle, syringe or introducer, as examples.

In some embodiments, the prosthetic disc need not have a reservoir 910. Rather, the resilient core could include the medication as part of its material makeup, such that the medication is released into the body over time.

Figure 9B:
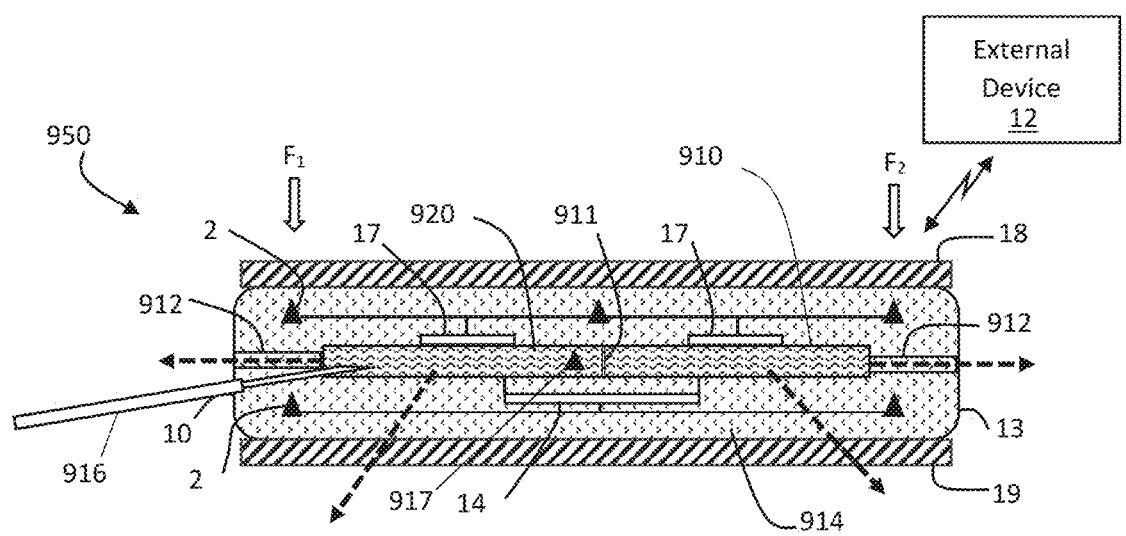
FIG. 9B is a side view of a prosthetic disc having an therapeutic delivery system in accordance with aspects of the inventive concept.

FIG. 9B is an embodiment of a prosthetic disc 950 similar to the prosthetic disc 900 of FIG. 9A. In this embodiment, the prosthetic device 950 is a sensing artificial disc having sensing electronics 14 and sensors 2, as well as one or more mechanisms 17 configured to control, influence, or alter conditions of the resilient core 10. In some embodiments, the mechanisms 17 are responsive to a medication signal from the sensing electronics 14 to cause the reservoir(s) 910 to release medication(s) 920 as discussed above. In some embodiments, the mechanisms 17 can include a heating element, wherein heating the reservoir(s) 910 and medication(s) 920 causes the medication to be less viscous or thinner so that it more easily flows or seeps through the resilient core 10 and into the body. In some embodiments, the mechanisms 17 can include a pressure-applying element, such as one or more piezo elements, configured and arranged to apply pressure to the reservoir(s) 910 to cause the medication(s) 920 to flow or seep through the resilient core 10 and into the body. In some embodiments, the medication signal is generated is response to a condition sensed by one or more of the sensors 2. In some embodiments, the medication signal is generated by an external device 12 in communication with the sensing electronics 14 and/or the mechanisms 17. That is, the external device 12 could send a signal to the sensing electronics and/or the mechanisms 17 that cause the mechanisms 17, e.g., a heat element and/or a pressure-applying element, to release medication(s) 920 from the reservoir(s) 910.

In disc 950, the reservoir 910 can be refillable, in some embodiments. In such cases, a medication delivery apparatus 916 can be used to add medication to the reservoir. The medication delivery apparatus 916 can take the form of a medical needle, syringe or introducer, as examples. A medication sensor 917 can be included to sense the level of available medication 920 in reservoir 910. When the level gets low, e.g., below a predetermined amount or threshold, the sensing electronics 14 can send a signal to external device 12 to prompt the addition of more medication. For example, external device 12 could be a mobile device (e.g., smartphone) of the person within which the prosthetic disc was implanted. The mobile device 12 could include an application that alerts the user and/or the user's healthcare provider to the sensed condition.

The therapeutic delivery system of FIGS. 9A and 9B, which includes the reservoir(s) 910 and medication(s) 920, and optionally the semipermeable material 914 of the resilient core 10 and/or the channels 912 can be implanted in any of the prosthetic discs disclosed herein, or any other form of prosthetic disc, such as those known and used between vertebrae.

Figure 10:
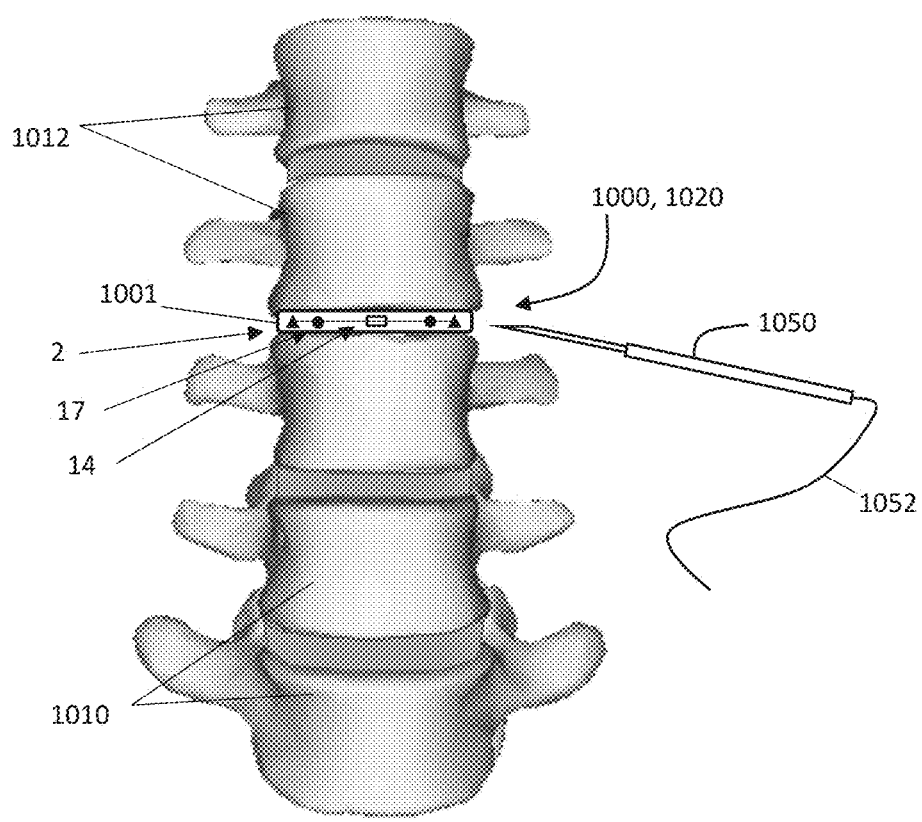
FIG. 10 is an embodiment of sensing electronics and sensors that can be added to, removed from, or replaced is an implanted prosthetic disc in accordance with aspects of the inventive concept.

FIG. 10 is an embodiment of a sensing electronics and sensors that can be added to an implanted prosthetic disc 1000, such as through an introducer. In FIG. 10, a plurality of vertebrae 1012 are shown. Natural discs 1010 are shown between several of the vertebrae 1012. But a prosthetic disc 1000 is shown between two of the vertebrae 1012. In FIG. 10, an introducer 1050 can be used to add sensing electronics 14, sensors 2 and mechanisms 17 to an already implanted disc 1001 to form a sensing artificial disc 1000.

A method of adding a sensing system 1020 comprising the sensing electronics 14 and sensors 2 (and optionally mechanisms 17) to an implanted disc 1001 include loading the sensing system into an introducer, components of the sensing system can include attachment or securing means, devices, or materials, such as adhesives. Inserting the introducer 1050 into the body such that a tip of the introducer is proximate the implanted disc 1001. Using the introducer 1050, delivering the sensing system 1020 to contact and secure to the implanted disc 1001. The method can include distributing one or more sensors 2 to different locations on or in the disc 1001. The locations of the sensors can be on a surface of the disc 1001 and/or inside the disc. The method can include delivering the sensing electronics to a surface 13 of the disc 1001 and/or inside the disc 1001. The method can include delivering mechanisms 17 to a surface 13 of the disc 1001 and/or inside the disc 1001. A wire 1052, as delivery mechanism, can be used as a mechanism for delivering the sensing system 1020, or its elements, through the introducer 1050 to the disc 1001. If components of the sensing system 1020 are delivered to an interior of the disc 1001, then the attachment or securing means, devices, or materials need not be necessary. Although, in some embodiments, such a glue or filler material may be used to close any punctures in the disc 1001 caused by the introducer. Accordingly, a sensing artificial disc 1000 is formed.

A method of removing a sensing system 1020 from a sensing artificial disc 1000 included inserting the introducer 1050 into the body such that a tip of the introducer is proximate the implanted sensing artificial disc 1000. Using the introducer 1050 one or more elements of the sensing system 1020 is engaged, whether on the surface of or internal to the disc 1000. The method can include drawing one or more elements of the sensing system 1020 through the introducer and external to the body. The drawing can occur through suction and/or through securing such elements to a removal mechanism 1052 fed through the introducer 1050. The removal mechanism 1052 can take the form of a wire. The wire 1052 can include an anchor, barb, hook, or other form of securing or gripping mechanism useful for securing elements of the sensing system 1020, e.g., for removal. Therefore, wire 1052 can be used as a delivery mechanism and a removal mechanism, in various embodiments.

In some embodiments, the introducer 1050 (and wire 1052) can be used to remove a sensing system element and replace it, or to simply add elements or remove them. For example, the introducer 1050 could be used to replace a battery or microprocessor of the sensing electronics 14 or add or replace sensors 2, as examples.

While the foregoing has described what are considered to be the best mode and/or other preferred embodiments, it is understood that various modifications can be made therein and that the invention or inventions may be implemented in various forms and embodiments, and that they may be applied in numerous applications, only some of which have been described herein. It is intended by the following claims to claim that which is literally described and all equivalents thereto, including all modifications and variations that fall within the scope of each claim.

It is appreciated that certain features of the invention, which are, for clarity, described in the context of separate embodiments, may also be provided in combination in a single embodiment. Conversely, various features of the invention which are, for brevity, described in the context of a single embodiment may also be provided separately or in any suitable sub-combination.

For example, it will be appreciated that all of the features set out in any of the claims (whether independent or dependent) can be combined in any given way.

What is claimed is:

1. A prosthetic intervertebral disc, comprising:
   a resilient core having a vertebrae-contacting top surface, a vertebrae-contacting bottom surface, and at least one sidewall;
   at least one sensor disposed in or on the resilient core, the at least one sensor including one or more sensors configured to measure a magnitude and a direction of compression of the resilient core;
   at least one processor operatively coupled to the at least one sensor and configured to process data, information, and/or signals from the at least one sensor;
   at least one mechanism configured to control, influence, or alter conditions of the resilient core as a function of the magnitude and the direction of the compression; and
   a wireless transmitter configured to transmit a signal based on the magnitude and direction of the compression,
   wherein the at least one mechanism comprises a stiffness control device that is adjustable to modify a stiffness of the resilient core,
   wherein the stiffness control device includes at least one heating element configured to raise a temperature of at least one region of the resilient core based on the magnitude and the direction of compression,
   wherein raising the temperature of the at least one region of the resilient core will change the softness and/or pliability of said at least one region of the resilient core.

2. The prosthetic intervertebral disc of claim 1, wherein the at least one sensor is embedded in the resilient core.

3. The prosthetic intervertebral disc of claim 1, comprising at least two sensors that are disposed in or on the at least one side wall of the resilient core.

4. The prosthetic intervertebral disc of claim 1, wherein the at least one sensor includes at least one strain gauge sensor.

5. The prosthetic intervertebral disc of claim 1, wherein the at least one sensor includes at least one temperature sensor.

6. The prosthetic intervertebral disc of claim 1, wherein the at least one sensor includes at least one sensor configured for wireless charging.

7. The prosthetic intervertebral disc of claim 1, wherein the signal representative of the magnitude and direction of compression is wirelessly transmitted to an external device.

8. The prosthetic intervertebral disc of claim 1, wherein the at least one heating element includes one or more heating elements configured to raise a temperature of a plurality of different regions of the resilient core.

9. The prosthetic intervertebral disc of claim 8, wherein the one or more heating elements includes at least one heating element ring.

10. The prosthetic intervertebral disc of claim 9, wherein the at least one heating element ring includes a plurality of concentric heating element rings.

11. The prosthetic intervertebral disc of claim 10, wherein at least two of the concentric heating element rings are independently controllable.

12. The prosthetic intervertebral disc of claim 1, wherein the stiffness control device further includes at least one piezo element.

13. The prosthetic intervertebral disc of claim 1, wherein the stiffness control device further includes an adjustable band or strap.

14. The prosthetic intervertebral disc of claim 1, wherein the stiffness control device is adjustable using an electromagnet.

15. The prosthetic intervertebral disc of claim 1, wherein the resilient core includes a semipermeable material configured to release a medication external to the resilient core.

16. The prosthetic intervertebral disc of claim 1, further comprising:
   a medication disposed within the resilient core, wherein the resilient core is configured to release the medication based on the magnitude and direction of the compression.

17. The prosthetic intervertebral disc of claim 1, further comprising:
   a medication maintained in at least one reservoir disposed within the resilient core;
   a medication sensor configured to sense a level of medication in the at least one reservoir; and
   wherein the wireless transmitter is configured to transmit a signal indicating a level of the medication in the at least one reservoir.

18. The prosthetic intervertebral disc of claim 17, wherein the at least one reservoir is refillable.

\* \* \* \* \*